United States Patent [19]

Nozaki, Jr. et al.

[11] Patent Number: 4,667,830
[45] Date of Patent: May 26, 1987

[54] METHOD AND MEANS FOR SORTING INDIVIDUAL PARTICLES INTO CONTAINERS FOR CULTURING, CLONING, ANALYSIS, OR THE LIKE

[75] Inventors: Tom Nozaki, Jr.; Richard G. Sweet; Richard T. Stovel, all of Palo Alto; David R. Parks, San Francisco, all of Calif.

[73] Assignee: The Board of Trustees of the Leland Stanford Junior University, Stanford, Calif.

[21] Appl. No.: 273,750

[22] Filed: Jun. 15, 1981

[51] Int. Cl.$^4$ .............................................. B07C 5/342
[52] U.S. Cl. .................................... 209/3.1; 209/579; 356/39; 356/72
[58] Field of Search .................................. 209/3.1–3.3, 209/571, 576–579; 356/39, 72, 73; 250/222 PC; 346/75; 250/461.2

[56] References Cited

U.S. PATENT DOCUMENTS

| | | | |
|---|---|---|---|
| 3,710,933 | 1/1973 | Fulwyler et al. | 209/579 X |
| 3,790,760 | 2/1974 | Stiller | 235/92 PC |
| 3,826,364 | 7/1974 | Bonner et al. | 209/579 X |
| 3,924,947 | 12/1975 | Hogg | 356/39 |
| 4,009,435 | 2/1977 | Hogg | 356/39 X |
| 4,148,718 | 4/1979 | Fulwyler | 209/579 X |
| 4,347,935 | 9/1982 | Merrill | 209/579 X |

OTHER PUBLICATIONS

Stovel and Sweet, Individual Cell Sorting, The Journal of Histochemistry, vol. 27, No. 1, pp. 284–288, 1979.
Parks, Bryan, Oi, and Herzenberg, Antigen-Specific Identification and Cloning of Hybridomas with Fluorescence-Activated Cell Sorter, Proc. Natl. Acad. Sci., U.S.A., vol. 76, No. 4, pp. 1962–1966, Apr. 1979, Genetics.

Primary Examiner—Randolph A. Reese
Assistant Examiner—Edward M. Wacyra
Attorney, Agent, or Firm—Victor R. Beckman

[57] ABSTRACT

Method and apparatus for sorting individual particles into containers, such as the wells of a microculture tray, are disclosed. The particles may comprise, for example, individual biological cells which then may be cultured, cloned, analyzed, or the like. The particles are incorporated into a flow stream which is jetted from a nozzle which is vibrated in the direction of the stream to break the jet stream into discrete drops. A particle sensor senses particles in the stream, and a signal processor in response to the particle sensor output produces an output when the sensed particle is of the type to be sorted from the stream. A pulse charger, responsive to the signal processor, is included for charging the drops as they break from the vibrating jet stream. The drops pass between charged deflection plates where they are deflected an amount related to the drop charge. For individual cell sorting, the signal processor is in normal inopertive condition to prevent sorting of drops from the drop stream. During this time all drops contained in the stream are caught by a stream catcher, and none are allowed to enter a tray well. When armed, by manual actuation of an arming switch, the circuit is conditioned to sort a single particle from the drop stream, at which time the circuit returns to normal inoperative condition. A tray support is provided for movable support of the multiwell tray along perpendicular X and Y directions, and a releasable detent releasably lock the tray support at any desired X-Y position. The tray support is provided with a target for use in initial alignment of the tray support relative to drops separated from the stream to assure entry of such drops into a tray well during subsequent operation of the cell sorter.

30 Claims, 9 Drawing Figures

METHOD AND MEANS FOR SORTING INDIVIDUAL PARTICLES INTO CONTAINERS FOR CULTURING, CLONING, ANALYSIS, OR THE LIKE

ORIGIN OF THE INVENTION

This invention was made with government support under Grant GM 17367 awarded by the Department of Health and Human Services. The Government has certain rights in this invention.

BACKGROUND OF THE INVENTION

Scanning devices for analyzing liquid samples delivered thereto and sorting particles such as biological cells contained therein according to sensed characteristics thereof are known as shown, for example, in U.S. Pat. No. 3,826,364, Bonner et al, which patent is assigned to the assignee of the present invention. Flow cell sorters of this type are designed to provide a large number of cells of a given subpopulation. Other cell sorting systems, such as shown in U.S. Pat. Nos. 3,924,947 and 4,009,435, and in an article entitled Individual Cell Sorting by Stovel and Sweet, The Journal of Histochemistry, Vol. 27, No. 1 pp. 284–288, 1979, move a collecting surface or tray beneath a charged droplet sorter so that deflected droplets are laid down sequentially in a scanning pattern. Often, prior art devices of this type require complicated, and expensive, moving means for accurately moving the surface or tray onto which the individual cells are sorted, and elaborate control circuitry for the control thereof. Also, the broad idea for operating a particle sorter to deposit a single particle into a manually positionable multiwell tray to collect individual particles in the tray wells is contained in an article entitled Antigen-Specific Identification and Cloning of Hybridomas with Fluorescence-activated Cell Sorter (FACS) by D. R. Parks, V. M. Bryan, V. T. Oi and L. A. Herzenberg, Proc. Natl. Acad. Sci. USA, Vol. 76, No. 4, pp. 1962–1966, April 1979, Genetics.

SUMMARY OF THE INVENTION AND OBJECTS

It is a general object of this invention to provide an improved particle sorting apparatus and method of simple design whereby single particles, such as physiological cells, may be simply and readily sorted into containers for culturing, cloning, analyzing, or the like.

Another object of this invention is to provide a particle sorting apparatus and method of the foregoing type which operate semiautomatically with a minimum amount of hardware for proper positioning of the container at a target area, and wherein each particle sorting operation is initiated under operator control.

The above and other objects and advantages of this invention are achieved by use of a flow type particle sorting system whereby particle containing liquid is jetted from a nozzle which is vibrated to break the stream into uniform discrete drops. Particle sensing means are provided for making one or more measurements on the particles contained in the stream. The signal, or signals, from the particle sensing means are processed to provide a signal output when a particle of the type to be sorted is sensed. Drop charging means are connected to the stream to charge the drop containing said particle with a desired charge. The drops pass through an electric field for relative deflection of the drops according to the amount of charge. Under normal operating conditions the drop charging means is prevented from changing the charge supplied to the stream, during which time all drops within the stream are collected by a stream catcher. The normally inoperative sorter is conditioned, or armed, by a pulse control signal to condition the sorter for sorting a single particle from the stream in response to a processed signal from the particle sensing means. The control signal is initiated under control of the operator, as by momentary closure of an arming switch, for example, whereupon the sorter is conditioned for particle sorting until a single particle to be sorted is in fact sensed and sorted from the stream.

The multiwell tray into which particles are sorted is positioned on a tray support which is movable along perpendicular X and Y directions by use of movable X and Y carriages. The tray support is releasably fastened to one of said first and second carriages, and releasable detent means releasably lock said carriages in position along the X-Y directions. The tray support is provided with a target for use in initial alignment of the tray support relative to drops separated from the stream. By releasing the fastening means which connect the tray support to one of the carriages, the tray support target is movable into proper alignment with drops separated from the drop stream. When in proper alignment, the fastening means is retightened. Now, all tray wells are properly alignable at a target area to receive drops separated from the drop stream. The tray support is movable by the operator following each particle separation for loading of a single particle into each of said wells. The steps of locating a tray well at the target area and conditioning the sorter for sorting operation are repeated under operator control until a desired number of wells are supplied with a single particle of the desired type.

BRIEF DESCRIPTION OF THE DRAWINGS

The invention, together with other objects and advantages thereof will be more fully apparent and understood from consideration of the following description in light of the drawings. In the drawings, wherein like reference characters refer to the same parts in the several views.

As mentioned above, prior art flow cell sorters which provide for the collection of fractions containing large numbers of particles are well known including, for example, a fluorescence-activated cell sorter of a type manufactured by Becton, Dickinson and Company (Becton, Dickinson FACS Division, Mountain View, Calif.) identified as FACS II, certain features of which sorter are disclosed in the above-identified U.S. Pat. No. 3,826,364. For purposes of illustration and description only, and not by way of limitation, the present invention will be described in terms of modifications to such FACS II cell sorter to adapt the same for individual cell sorting.

Figure 1:
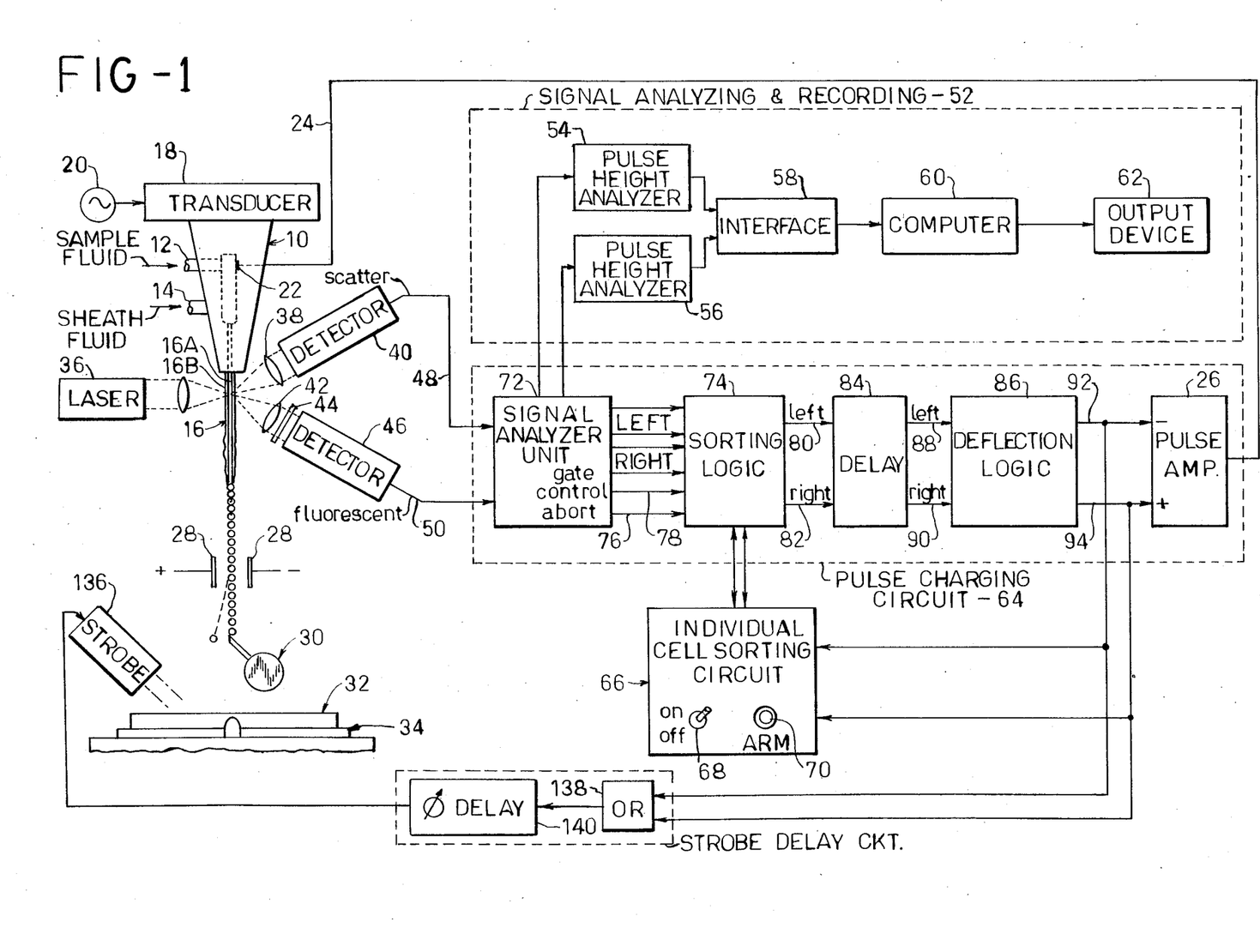
FIG. 1 diagrammatically shows a particle sorter embodying the present invention, which includes means for sorting a single particle into a container.

Reference first is made to FIG. 1 wherein a flow type particle scanning and sorting system is shown, comprising a nozzle assembly 10 which includes inner and outer coaxially located nozzles (not shown) supplied with sample and sheath fluid through conduits 12 and 14, respectively, from pressurized sources of such sample and sheath fluids, not shown. A coaxial stream 16 comprising an inner sample-containing portion 16A and outer particle-free sheath portion 16B emerges from the nozzle assembly 10. The nozzle assembly is vibrated in an axial direction by means of a transducer, such as piezoelectric crystal transducer 18, causing the jet stream to break into drops. An oscillator 20 energizes the transducer 18 for vibration of the nozzle assembly at a desired rate.

An electrode 22 is provided which is in contact with the electrically conducting, isotonic, sheath fluid. The electrode is connected over line 24 to the output from a pulse amplifier 26 for use in selectively charging drops as they break from the stream 16. The selectively charged drops pass through a transverse electrostatic field established by a pair of opposite deflection plates 28,28 connected to opposite polarity dc potential sources of, say, ±2500 volts, for the deflection of charged drops in an amount related to the drop charge. For individual particle sorting, a stream catcher 30 is located downstream from the deflection plates for collecting drops except those to be sorted from the stream. A multiwell tray 32, carried by a novel tray supporting means 34 of this invention, is used to collect drops separated from the stream. The stream catcher 30 and novel movable tray supporting means 34 are described in greater detail hereinbelow.

Particle sensing means for making one or more measurements on particles contained in the sample fluid at the inner stream portion 16A of the coaxial stream 16 are provided. With the present system all particles are sensed, and those particles to be separated from others are uniquely identified. For purposes of illustration, the particle sensing means is shown comprising one means for detecting all particles entrained in the fluid stream, and a second means for the detection of selected particles, here, fluorescent particles. A laser 36 having a beam focused on the inner coaxial stream illuminates particles contained therein. Illumination scattered from illuminated particles is focused by lens 38 onto the face of a detector 40 for the detection of all particles contained in the stream. The particles are treated to render selected ones fluorescent and the laser excites said selected particles to fluorescence. The fluorescent light from said selected particles is directed through focusing lens 42 and filter 44 onto the face of a detector 46 for detection of such particles. Treatment of particles, such as certain biological cells, to render selected ones fluorescent is well known and requires no additional description. With the illustrated arrangement, it will be apparent that all particles contained in the inner stream including fluorescent particles, are detected by detector 40 to provide an output at scatter channel 48, whereas the fluorescence, if any, of each particle is detected by detector 46 to provide an output at fluorescence channel 50.

For particle sorting, the scatter and fluorescent channel signals are supplied to a pulse charging circuit 64 which processes the signals and supplies an output to the drop charging electrode 22 from the pulse amplifier 26. This circuit may be of substantially conventional design, and may be of the type employed in the above-mentioned FACS II sorter. Normally, the pulse charging circuit 64 operates to sort selected particles from the stream 16 into a container to provide a large number of such particles therein. With the present invention, operation of the charging circuit unit 64 is modified for separation of a selected individual particle from the stream, after which sorting operation is disabled until another container, or tray well, is located to receive another selected particle. Under operator control, the pulse charging circuit unit is enabled for separation of another selected particle from the stream. A unit 66, labeled Individual Cell Sorting Circuit, of this invention interfaces with the pulse charging circuit 64 to selectively modify operation of the circuit 64 for individual cell sorting operation when desired. An on-off switch 68 at the unit 66 is used to switch between normal and individual particle sorting operations, and an arming switch 70 conditions the circuit for separation of a single particle from the stream when momentarily actuated. The individual cell sorting circuit 66 is described in detail hereinbelow. First, however the pulse charging circuit unit 64 will be described.

The scatter and fluorescent channel signals from detectors 40 and 46 are supplied to a signal analyzer unit 72 which includes a plurality of single channel analyzers with adjustable windows. The illustrated signal analyzer 72 includes four (4) single channel analyzers, two of which are responsive to scatter channel signals, and two of which are responsive to fluorescent channel signals. Scatter and fluorescent signals from one pair of single channel analyzers are supplied to a sorting logic unit 74 over a left channel, while scatter and fluorescent signals from the other pair of single channel analyzers are supplied to the sorting logic unit over a right channel. Additionally, abort and trigger signals are obtained from the analyzer unit 72 and supplied to the sorting logic unit 74. An abort signal is produced by the analyzer 72 at output line 76 whenever scatter channel inputs thereto occur too close in time to allow proper processing of signals from the later-detected particle. A gate control signal is produced at line 78 from the analyzer 72 whenever a scatter channel input is received from detector 40. The abort and gate control functions are described in greater detail hereinbelow with reference to FIG. 2A.

As noted above, the individual cell sorting circuit 66 also interfaces with the sorting logic unit for control thereof when the sorter is used for individual cell sorting. With switch 68 in the off position, the sorting logic unit 74 functions to provide a Sort signal output at the left channel output line 80 when left channel S (scatter) and F (fluorescent) signals simultaneously are present at the input thereto. Similarly, a Sort signal output is provided at the right channel output line 82 when right channel S and F signals simultaneously are present at the input thereto. In the presence of an abort signal at line 76 from the analyzer unit 72, simultaneous left and right channel signals are produced at the output lines 80 and 82 from the sorting logic unit. Similarly, the presence of signals from a particle which do not satisfy the scatter and fluorescence criteria for either the right or left channel results in the production of simultaneous left and right channel signals at the output lines 80 and 82 of the sorting logic unit 74.

The left and right channel Sort signal outputs from the sorting logic unit are supplied to a delay unit 84 which includes separate left and right channel delay elements, such as shift registers, through which left and right channel Sort signals, respectively, pass. From the shift register delays, the delayed left and right channel Sort signals are supplied to a deflection logic unit 86 over lines 88 and 90, respectively. With a delayed left channel Sort signal at line 88 to the deflection logic unit, an output Trigger pulse is provided at line 92 therefrom; and with a delayed right channel Sort input signal at line 90, an output Trigger pulse is provided at line 94 therefrom. With simultaneous delayed left and right channel Sort input signals to the deflection logic unit 86, no Trigger output is provided at either line 92 or 94.

The Trigger outputs from the deflection logic unit 86 are used to trigger the pulse amplifier 26 which, as noted above has an output connected to the electrode 22 for drop charging. With a left channel Trigger signal to the pulse generator at line 92, the pulse amplifier 26 has a negative pulse output which, when applied to the flow stream 16 results in drop deflection to the left, as viewed in FIG. 1. Similarly, with a right channel Trigger signal at line 94 to the pulse amplifier, a positive pulse is produced at the output to provide drops breaking from the stream 16 with a positive charge for deflection thereof to the right upon passing between deflection plates 28,28. In the illustrated arrangement, wherein the drop catcher is located to the right of the stream 16, only left channel Trigger signals are employed for drop deflection to the left during individual cell sorting operation. Obviously, for normal sorting operation, the stream catcher 30 is removed, and the switch 68 is placed in the off position thereby allowing for drop deflection to the left and/or right. Alternatively, a centrally-located stream catcher, not shown, may be employed which may be left in place at all times, including operation during left and right sorting.

Outputs from the signal analyzer unit 72 may be supplied to a signal analyzing and recording unit 52 for analysis and recording of detected signals produced by all particles. Unit 52 is shown comprising multichannel pulse height analyzers 54 and 56 to which signals from the signal analyzer unit 72 are supplied and from which the pulse height spectrum of the signals are obtained. Outputs from the pulse height analyzers may be recorded or otherwise utilized, as desired. Here, the analyzer outputs are shown supplied through an interface 58 to data acquisition means comprising a computer 60 and associated output device 62, such as a printer, CRT terminal, or the like. With this arrangement, measurements may be made on all detected particles contained in the flow stream, including particles separated from the stream.

Figure 2A:
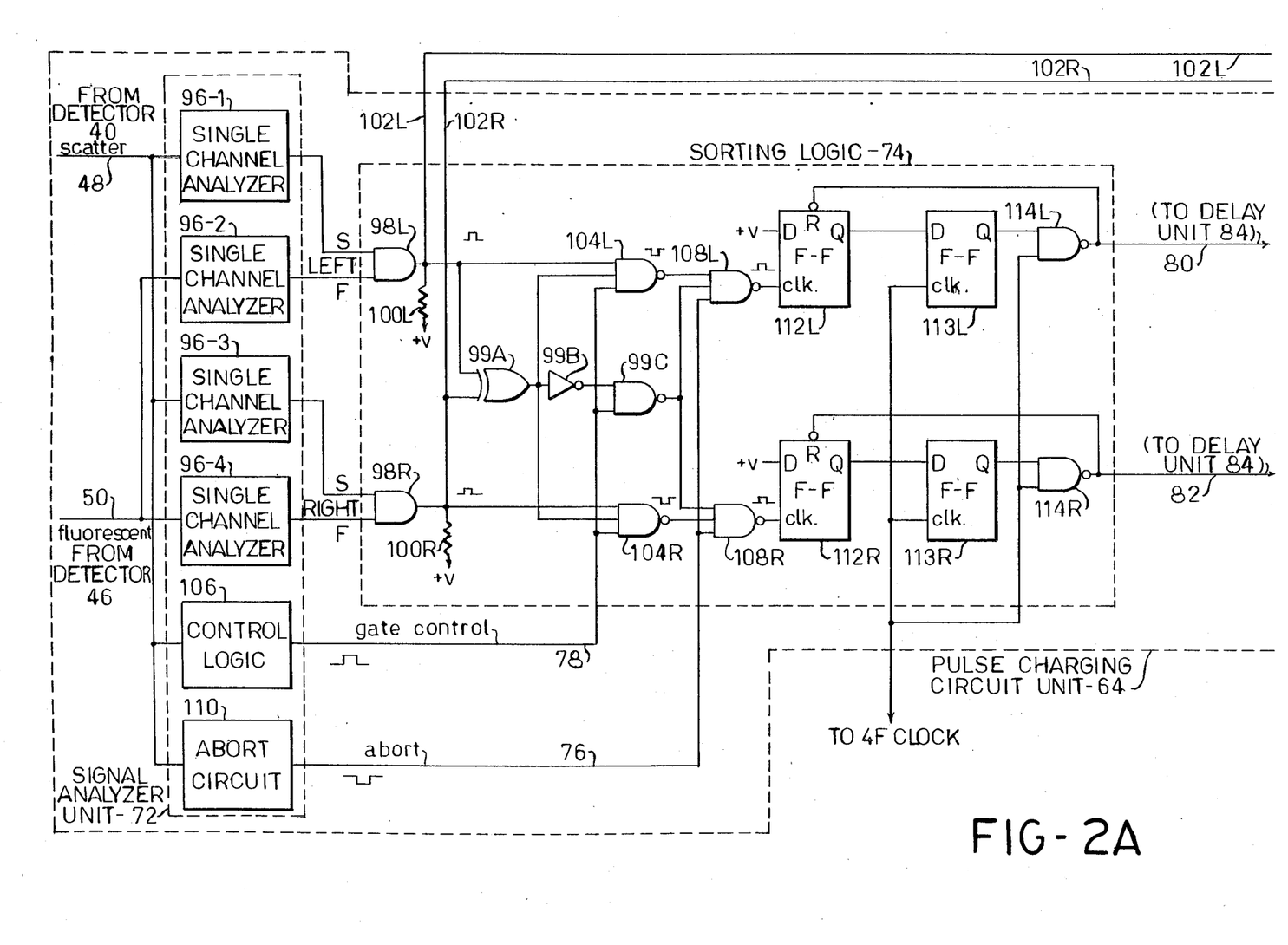
FIGS. 2A and 2B together show in greater detail circuitry employed in the sorter shown in FIG. 1.

Reference now is made to FIG. 2A wherein a portion of the pulse charging circuit unit 64, including the signal analyzer unit 72 and sorting logic unit 74, is shown in greater detail. The above-mentioned four single channel analyzers included in the signal analyzer unit 72 are shown in FIG. 2A and identified by reference characters 96-1, 96-2, 96-3 and 96-4. Scatter signals from photodetector 40 are supplied to single channel analyzers 96-1 and 96-3, while fluorescent channel signals from detector 46 are supplied to single channel analyzers 96-2 and 96-4. Each analyzer has an adjustable window which may be set by the operator for sorting of selected cells. Scatter and fluorescent signals from analyzers 96-1 and 96-2, respectively, at the left channel, are supplied to AND gate 98L in the sorting logic unit 74, while scatter and fluorescent signals from analyzers 96-3 and 96-4, respectively, at the right channel, are supplied to AND gate 98R. It will be noted that AND gates 98L and 98R comprise open collector gates which allows for connection of the outputs thereof to outputs from other open collector gates included in the individual cell sorting circuit 66 shown in FIGS. 1 and 2B. External pull-up resistors 100L and 100R are provided which function as collector load resistors for the respective logic gates 98L and 98R, and other open collector logic gates included in the individual cell sorting circuit unit 66, described below.

For each detected particle which fits the window settings of single channel analyzers 96-1 and 96-2, a left channel Sort signal output is obtained from logic gate 98L, and for each detected particle which fits the window settings of single channel analyzers 96-3 and 96-4 a right channel Sort signal output is obtained from logic gate 98R. The left and right channel Sort signal outputs from gates 98L and 98R are connected over lines 102L and 102R to the individual cell sorting circuit 66 shown in FIG. 2B, and to exclusive OR gate 99A, and NAND gates 104L and 104R, respectively, in the sorting logic unit 74. The output from the exclusive OR gate 99A is supplied as a second, gate control, input to NAND gates 104L and 104R. A third input for NAND gates 104L and 104R is obtained from a control logic circuit 106 in the signal analyzer unit 72, to which circuit scatter signal pulses are supplied from detector 40. For every detected particle, a gate control pulse is produced at output line 78 from the control logic unit 106. If the other two inputs to the NAND gates 104L and 104R are high during the presence of the gate control pulse from unit 106, the NAND gate outputs change from a high to a low state. Otherwise, the NAND gate outputs remain high during gate control pulses. (It here will be noted that the input for the control logic unit 106 may be obtained from the fluorescence channel 50 rather than scatter channel 48 if all relevant particles also are detected by the fluorescence detector 46.) From the above, it will be seen that in the absence of scatter and fluorescent signals from detectors 48 and 50, or in the presence of such signals which do not satisfy the scatter and fluorescence criteria for either the right or left channel as established by the signal analyzers, the outputs from AND gates 98L and 98R remain low thereby preventing the outputs from NAND gates 104L and 104R from going low. In the presence of scatter and fluorescent signals from detectors 48 and 50 which satisfy the scatter and fluorescence criteria for either the right or left channel, the output from either AND gate 98L or 98R goes high, the output from exclusive OR gate 99A goes high, and a high gate control signal is produced by control logic unit 106 whereby the output from one of the gates 104L or 104R goes low.

The outputs from NAND gates 104L and 104R are supplied as inputs to NAND gates 108L and 108R, respectively. Second inputs for NAND gates 108L and 108R are obtained from exclusive OR gate 99A through an inverter 99B and a NAND gate 99C. Third gate inputs are provided from the abort circuit 110 over line 76. In the absence of any detected particles, all of the inputs to NAND gates 108L and 108R are high such that the gate outputs are low. A gate control signal from control logic unit 106 produced by detection of a particle in the jet stream provides a high at one input to NAND gate 99C. If the particle does not satisfy the scatter and fluorescence criteria for either the left or right channel, the output from exclusive OR gate 99A remains low. This low signal is inverted by inverter 99B, and the resultant high inverter output is supplied as a second input to the NAND gate 99C whereby the NAND gate output goes low. The low NAND gate output simultaneously is supplied to both of the NAND gates 108L and 108R whereupon the NAND gate outputs simultaneously switch from low to high.

As noted above, the abort circuit output also is supplied as inputs to the NAND gates 108L and 108R. The abort circuit has an output which normally is high. It includes threshold circuits for generation of a low abort signal output at line 76 whenever an input signal to the abort circuit occurs during the signal processing time of a signal produced by a previous particle. The low abort signal at the inputs to gates 108L and 108R simultaneously switch the gate outputs from low to high.

When the output from either gate 104L or gate 104R goes high (but not both gates simultaneously) the output from the corresponding left or right channel gate 108L or 108R switches from low to high.

The outputs from NAND gates 108L and 108R are supplied as clock input signals to flip-flops 112L and 112R, respectively. The data input terminals of the flip-flops are connected to a positive voltage source whereby the output changes from low to a high on the low to high transition of the outputs from the respective gates 108L and 108R.

The outputs from flip-flops 112L and 112R are connected to the D input terminals of flip-flops 113L and 113R, respectively, which are clocked by a system 4F clock which operates at a frequency four times that of the drop formation controlling oscillator 20 shown in FIG. 1. The outputs from the flip-flops 113L and 113R are connected through NAND gates 114L and 114R to shift registers 116L and 116R, respectively, (see FIG. 2B) in the delay unit 84. The other input terminals of gates 114L and 114R are supplied with an output from the 4F system clock to synchronize the gate outputs with the system clock. Outputs from the gates 114L and 114R also are supplied to the reset terminals of flip-flops 112L and 112R to reset the same after a flip-flop is clocked by an input thereto from NAND gate 108L or 108R.

Figure 2B:
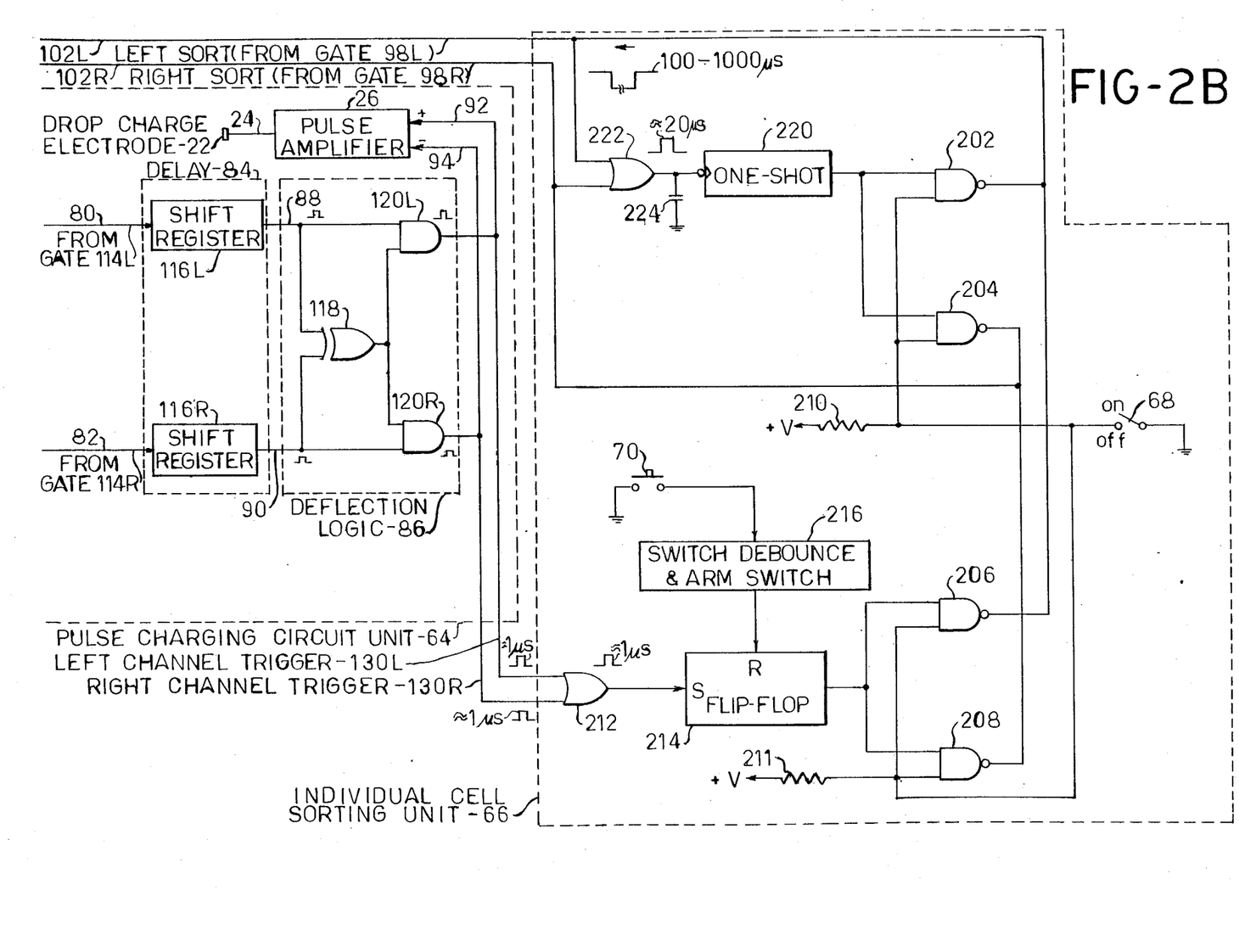

Referring to FIG. 2B, the shift registers 116L and 116R, which are clocked by the system 4F clock, provide the necessary time delays to allow for travel time of the particle from a point of detection to a point where the stream breaks into drops. From shift register delay unit 84, the delayed Sort signals are supplied over lines 88 and 90 to the deflection logic unit 86 which simply is shown to include an exclusive OR gate 118 and a pair of AND gates 120L and 120R. With an input pulse at line 88, but not at line 90, the exclusive OR gate output is high, whereby both inputs to AND gate 120L are high so that the output at line 92 is high. Similarly, with an input pulse at line 90, but not at line 88, the exclusive OR gate output is high and the output from the right channel AND gate also is high. However, with inputs at both input lines 88 and 90, as when an abort signal is produced at line 76 or when a particle is present which fulfills neither left or right sorting criteria, the output from the exclusive OR gate 118 remains low whereby the output from both gates 120L and 120R also remain low to prevent operation of the pulse amplifier 26 by the delayed SORT signals.

Figure 3:
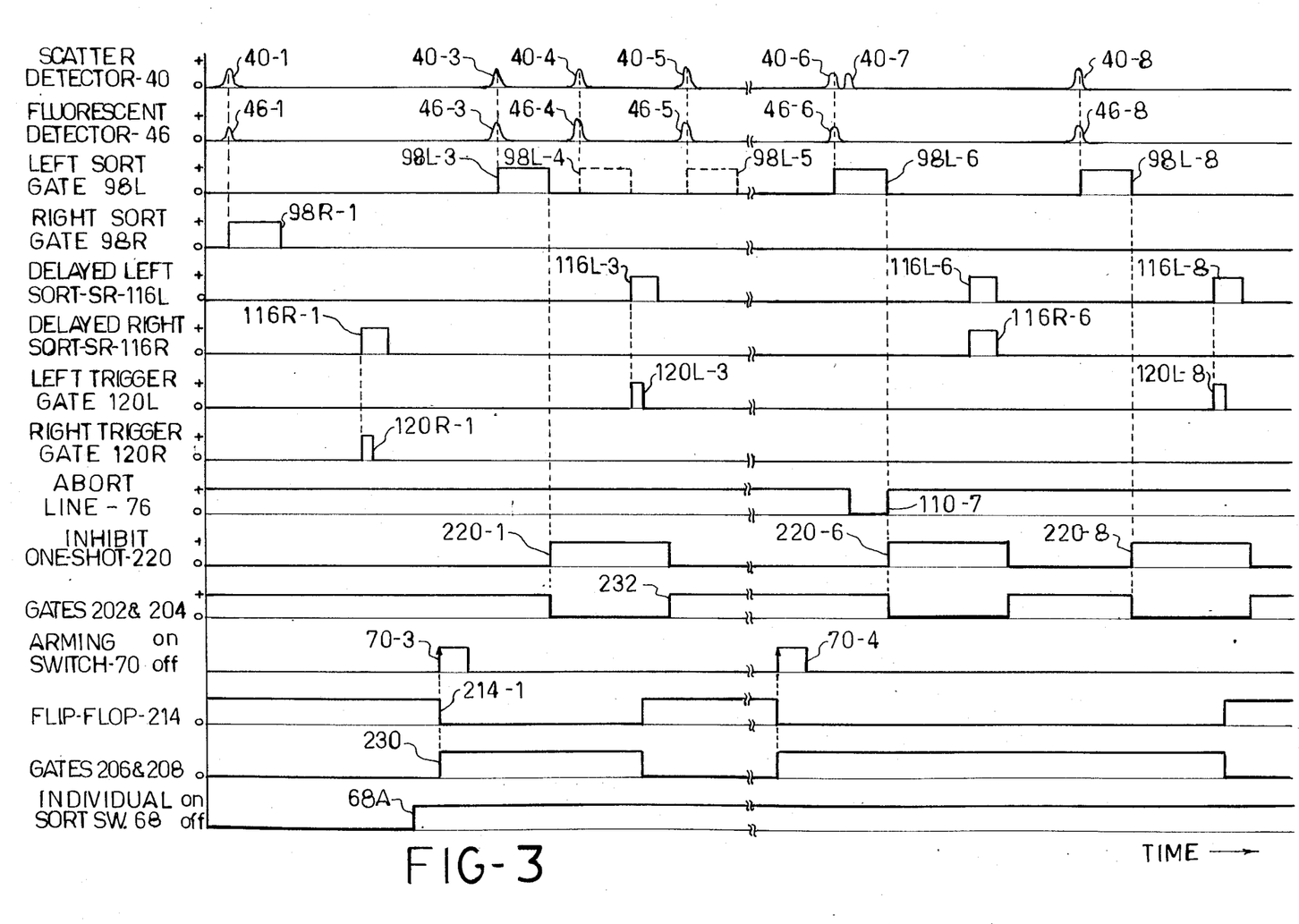
FIG. 3 shows a series of waveforms which occur at various points in the circuit of FIGS. 2A and 2B, for use in explaining the operation thereof.
Figure 4:
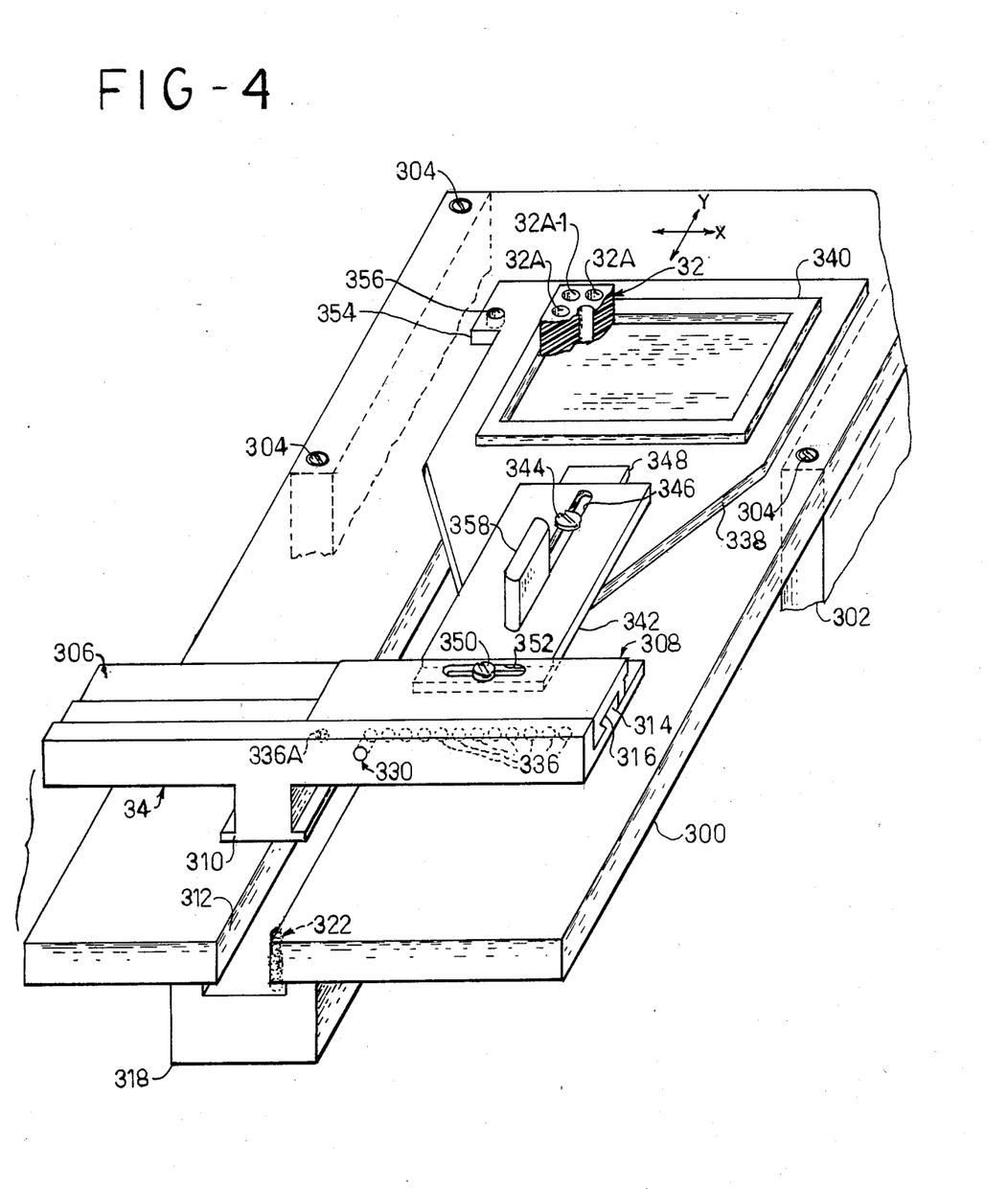
FIG. 4 is a fragmentary perspective view of a manually movable tray support system for use with the individual cell sorting system of the present invention.
Figure 5:
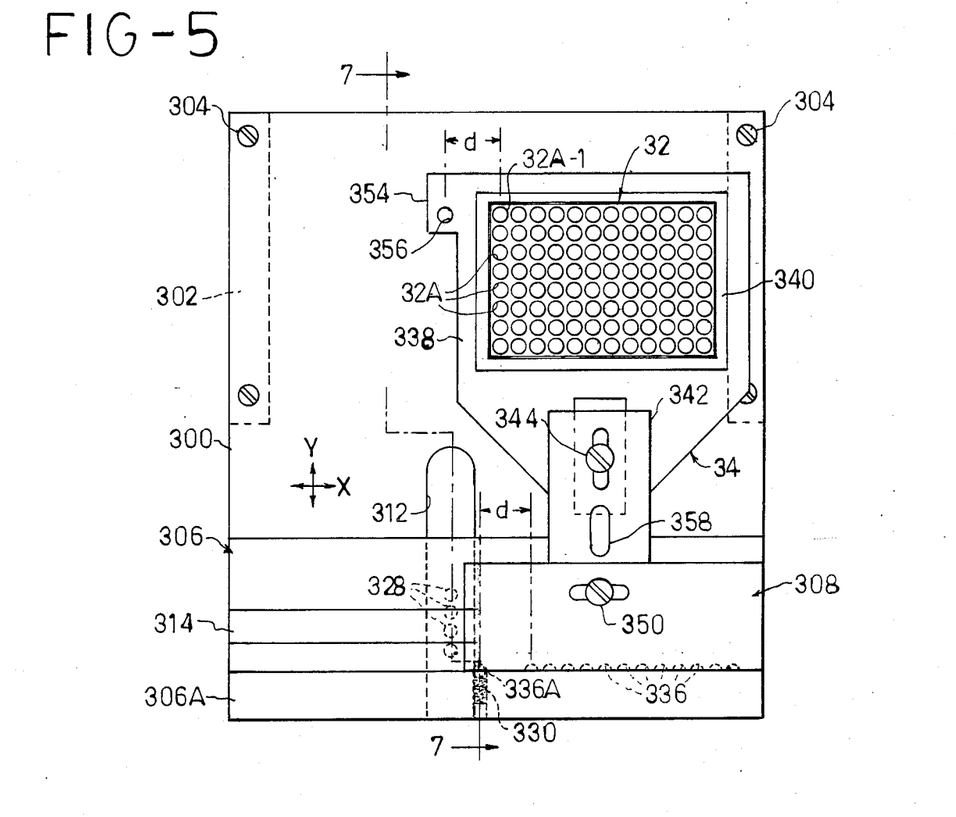
FIG. 5 is a plan view of the manually movable tray support system shown in FIG. 4.
Figure 6:
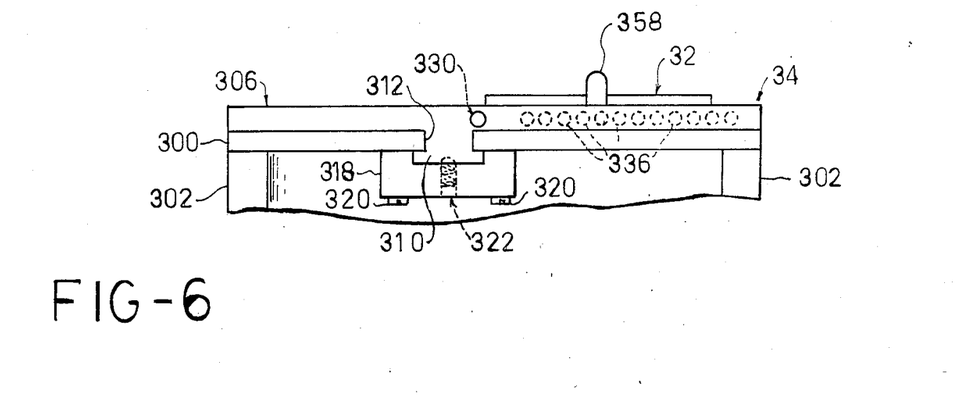
FIG. 6 is a front view of the manually movable tray support system shown in FIG. 5.
Figure 7:
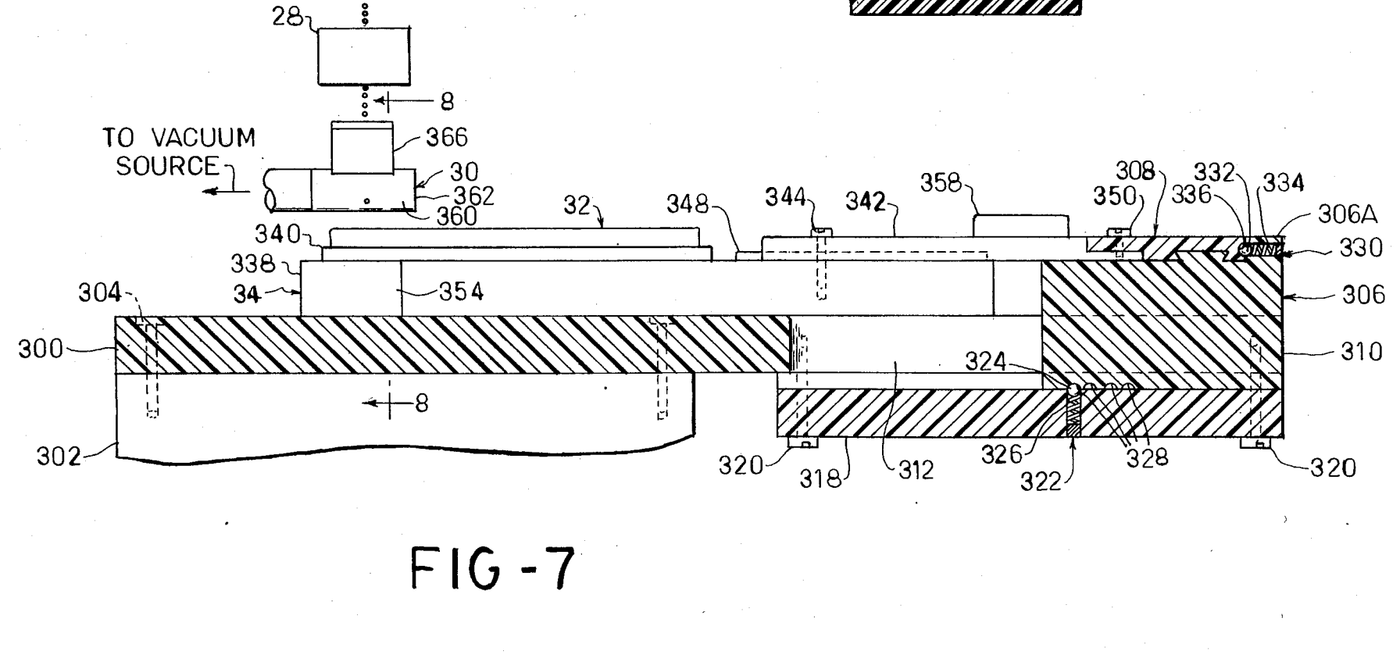
FIG. 7 is a sectional view of the manually movable tray supporting system, taken substantially along line 7—7 of FIG. 5 and also showing the stream catcher and one of the stream deflection plates positioned thereabove.
Figure 8:
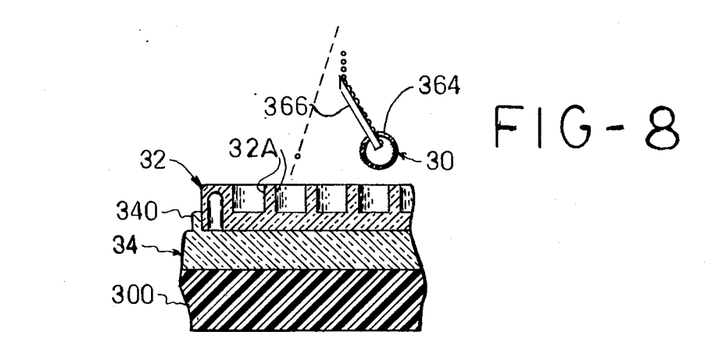
FIG. 8 is a sectional view taken substantially along line 8—8 of FIG. 7.

As noted above, with the switch 68 (FIG. 1) in the off position, the pulse charging unit 64 functions in a manner known in the prior art for sorting a plurality of particles of a selected type into a container. A brief description of such operation now will be given, with reference also to waveforms shown in FIG. 3, which will facilitate an understanding of the individual particle sorting operation described below. For prior art gross particle sorting operation, the stream catcher 30 is removed and a plurality of containers, not shown, are positioned to catch right-deflected, undeflected, and left-deflected drops after passing between the deflection plates 28,28. Windows of single channel analyzers 96-1 through 96-4 may be adjusted for sorting particles of one type to the left, and particles of another type to the right. Drops containing other particles are not charged and, therefore, pass undeflected between the deflection plates 28,28. A particle, or cell, contained in the jet stream is detected by scatter illumination received by the photodetector 40 and, if the cell is fluorescent, it also is detected by fluorescent luminescence received by the photodetector 46. Signal output pulses 40-1 and 46-1 from the detectors 40 and 46, respectively, are shown in the waveforms of FIG. 3. If the pulses fall within the selected amplitude limits of, say, analyzers 96-3 and 96-4, scatter and fluorescent signal pulses are generated by the analyzers, which pulses are applied to AND gate 98R, causing the output to go high. In the waveforms, the resultant output from the gate 98R is designated a right Sort pulse, and is identified by reference character 98R-1. There is no corresponding left Sort pulse output from AND gate 98L since both pulses 40-1 and 46-1 do not fit the windows of the respective analyzers 96-1 and 96-2.

The right channel Sort signal 98R-1 passes through the sorting logic circuit 74, the delay shift register 116R, the output from which register is identified by reference character 116R-1 in FIG. 3. The delayed right Sort pulse output from the shift register 116R activates AND gate 120R in the deflection logic 86 which results in a right channel Trigger signal 120R-1 therefrom to trigger the pulse amplifier 26. The resultant negative pulse output from the amplifier 26 is coupled to the drop charging electrode 22. The drop, or drops, breaking from the stream 16 during the presence of the amplifier output are charged, from subsequent deflection thereof when passing between the charged deflection plates 28,28. Here, the negative drop charge results in right deflection of the drops. In this manner, sorting continues until no more particle containing sample fluid is available.

As noted, the circuit shown in FIG. 2A and described above for sorting a plurality of particles into a container is known in the prior art. With electronic and mechanical modifications, now to be described, the apparatus is adapted for individual particle sorting. When operating in the individual particle sorting mode, it is convenient to deposit particles in individual wells of a multiwell container, such as the microculture tray 32 shown in FIG. 1. Mechanical modifications include use of the stream catcher 30 for collecting all drops except those sorted into a tray well, and use of a movable tray support 34 to facilitate proper location of the tray 32 relative to the deflected drop stream. First, the individual cell sorting circuit 66 shown in FIGS. 1 and 2B will be described.

In FIG. 2B, the operator controlled switch 68 for on-off control of the individual cell sorting circuit has one terminal connected to common ground and a second terminal connected to one input of a plurality of open collector NAND gates 202, 204, 206 ans 208. The outputs of logic gates 202 and 206 are connected together and through lead 102L to the output from the open collector gate 98L (FIG. 2A). Similarly, the outputs from the logic gates 204 and 208 are connected together and through the lead 102R to the output from open collector gate 98R (FIG. 2A). With the switch 68 in the off position, i.e. closed, NAND gates 202, 204, 206 and 208 each have one input which is low whereby the output from each gate is high. However, being open collector type gates, the outputs may be pulled low by outputs from open collector gates 98L and 98R shown in FIG. 2A. Consequently, with switch 68 in the closed, off, position, the gates 98L and 98R function in the manner described above for exclusive control of left and right channel Sorting pulses at lines 102L and 102R; the outputs from gates 202, 204, 206 and 208 having no control over the circuit operation.

With the switch 68 in the illustrated on position (i.e. open condition) one input of each of the logic gates 202, 204, 206 and 208 is in a high state as provided by a positive dc source connected to gate inputs through pull-up resistors 210 and 211. Now, the outputs from the gates 202, 204, 206 and 208 will be low when the other gate input also is high, for control of lines 102L and 102R. As will become apparent, open collector gates 202 and 204 are included in a circuit controlled by left and right channel Sort pulses for momentarily inhibiting operation of the left and right channel gates 98L and 98R while those left and/or right channel Sort pulses which actuated the circuit are propagating through the remainder of the sorting logic circuit 74, delay unit 84, and deflection logic circuit 86. The open collector gates 206 and 208, on the other hand, are included in another circuit which is controlled by Trigger pulses from the deflection logic circuit 86 for inhibiting operation of the gates 98L and 98R until such time that the said other circuit is manually reset.

Left and right channel Trigger pulses from gates 120L and 120R are connected over lines 130L and 130R to inputs of an OR gate 212 (FIG. 2B). The OR gate output is supplied to a flip-flop 214 to set the same. The flip-flop output, in turn, is supplied as a second input to the open collector NAND gates 206 and 208. In the flip-flop set condition, the flip-flop output is high whereupon the outputs from open collector gates 206 and 208 are low. The low open collector gate outputs pull lines 102L and 102 low, thereby preventing left and right Sort signals from being produced at the outputs of gates 98L and 98R, respectively. Under these conditions gate control signals produced at the output of control logic unit 106 upon detection of a particle will generate both left and right Sort signals at the outputs of NAND gates 108L and 108R via NAND gate 99C. As described above, the presence of both left and right Sort signals in the deflection logic circuit 86 prevents the particle from being sorted. It will be apparent, then, that once a right or left Trigger signal is produced, at the output from the deflection logic unit 86, for drop charging, the sorting circuit unit 64 is disabled until the flip-flop 214 is reset. Resetting of the flip-flop 214 is under control of the manually operated switch 70 which is shown connected to the reset input terminal of the flip-flop through a switch debounce and arm hold-off circuit 216. The circuit 216, which is of conventional design, includes a debounce circuit for debouncing the switch 70, and a hold-off circuit for preventing resetting of the flip-flop unit the switch 70 has been activated for, say, one second, to prevent premature accidental arming of the circuit. For convenience, the switch 70 may be foot-operated to free the operator's hands for other tasks.

When the flip-flop 214 is reset by momentary closure of the arming switch 70, the flip-flop output is low, which low output is supplied to the open collector gates 206 and 208. Now, with both inputs to the gates 206 and 208 low, the gate outputs are high. As noted above, the gate outputs (i.e. lines 102L and 102R) may be pulled low by the other open collector gates 202 and 204, or 98L and 98R. As is well understood the open collector gates 98L, 202 and 206 in the left channel together perform an AND operation, as do the open collector gates 98R, 204 and 208 in the right channel.

The open collector gates 202 and 204 are included in a circuit which is responsive to left and right Sort signals from gates 98L and 98R for momentarily preventing the sorting logic unit 74 from producing subsequent left or right channel Sort signals in response to outputs from the analyzers 96-1 through 96-4 immediately following said left or right Sort signal. Of course, simultaneous right and left channel Sort signals in response to outputs from control logic unit 106 or abort circuit 110 may still be produced at the output from the sorting logic unit 74. The open collector gates 202 and 204 are supplied with inputs from an adjustable one-shot multivibrator 220 which is triggered by the trailing edge of either a left or right channel Sort pulse supplied thereto through an OR gate 222. A filter capacitor 224 is included in the connection of the OR gate output to the input of the one-shot multivibrator 220 to prevent inadvertant triggering of the multivibrator 220 by noise signals. When triggered by the trailing edge of a left or right channel Sort pulse, the one-shot multivibrator 220 output goes high, whereupon the outputs from open collector gates 202 and 204 go low. As with gates 206 and 208, a low at the output of gates 202 and 204 pulls lines 102L and 102R low, thereby preventing subsequent left or right channel Sort pulses from being produced at the outputs of gates 98L and 98R. The open collector gate outputs are held low by outputs from gates 202 and 204 for a period of time determined by the length of the pulse from the one-shot. In practice, the period of time is adjusted to be somewhat longer than the shift register delay in unit 84 so that, if the original particle fulfilling the sorting criteria is not actually sorted thereby flip-flop 214, the outputs of gates 98L and 98R are released at the end of the period of one-shot 220 and a new particle may be accepted and sorted.

A brief description of the operation of the individual cell sorting unit 66 with reference to waveforms shown in FIG. 3 now will be provided. For individual cell sorting the stream catcher 30 (FIG. 1) is attached to the device by means not shown. In FIG. 1 the stream catcher 30 is shown positioned to catch all undeflected drops, and to allow for sorting of drops to the left. Obviously, the stream catcher may be mounted at the other side of the stream for right sorting. (Alternatively, a centrally located stream catcher may be used.) Windows of the left channel analyzers 96-1 and 96-2 (FIG. 2A) are adjusted for sorting of cells having the desired characteristics. Individual cell sorter switch 68 is turned on, as shown by waveform 68A in FIG. 3, for, essentially, enabling operation of open collector gates 202 and 204, and 206 and 208 in response to signals from the flip-flop 214 and one-shot 220, respectively. Before the actual collection on individual cells in wells of the multiculture tray 32 begins, the apparatus is operated several times during which the novel tray support 34, described in detail below, is properly aligned with the stream 16 to assure that drops deflected from the stream will enter the wells of the multiculture tray 32. Any left or right Trigger pulse from deflection logic unit 86 occuring during each preliminary operation functions to set the flip-flop 214, which remains in the set condition until reset by operation of switch 70. With switch 68 on, and the flip-flop 214 output 214-1 high, the output waveform 230 from open collector gates 206 and 208 is low thereby preventing outputs from gates 98L and 98R from going high. The production of left (or right) channel Sort pulses now is thereby prevented, to prevent any sorting operation.

With the multiculture tray 32 properly aligned relative to the drop stream 16, the arming switch 70 is momentarily actuated to condition the circuit for sorting a single particle from the stream into the selected tray well. Upon actuation of the arming switch 70, is indicated by pulse 70-3, the flip-flop 214 is reset, as shown by flip-flop output 214-1. With a low at one input of open collector gates 206 and 208, the gate outputs go high as indicated by waveform 230. Now, the outputs from gates 98L and 98R (FIG. 2A) no longer are held low, whereby the gates are free to produce left or right channel Sort pulses in response to analyzer outputs. (As noted above, sorting to the left only is provided with the stream catcher 30 located in the illustrated position.)

Detector outputs 40-3 and 46-3 from detectors 40 and 46 which fit the window settings of the left channel analyzers 96-1 and 96-2 produce a left channel Sort signal 98L-3 at the output from the open collector gate 98L. The one-shot 220 is triggered by the trailing edge of the left channel Sort signal 98L-3, as indicated by waveform 220-1. The one-shot output supplied to inputs of gates 202 and 204 produces a low at the gate outputs which pulls the lines 102L and 102R low to prevent generation, or production, of left or right channel Sort signals from the open collector gates 98L and 98R for the duration of the one-shot output. In FIG. 3, the outputs from gates 202 and 204 are identified by reference numeral 232. The one-shot output pulse is of sufficient length to allow for travel of the Sort signal 98L-3 through the circuit, including delay 84, to the pulse amplifier 26, before the end of the one-shot pulse. Any particles detected during this time, such as the particle which produces detector outputs 40-4 and 46-4, are prevented from producing a Sort signal at the output from gate 98L or 98R by reason of the low output 232 from gates 202 and 204 applied to the output lines 102L and 102R from the gates.

When the left Sort pulse 98L-3 propagates through the circuit and produces a delayed Sort pulse output 116L-3 from the left shift register delay 116L and a left Trigger pulse 120L-3 from the deflection logic unit 86, the flip flop 214 is set by said Trigger pulse connected thereto over line 130L and gate 212. The high output from the flip-flop 214 causes the outputs 230 from gates 206 and 208 to go low to continue to hold lines 102L and 102R low. Now, when the one-shot output 220-1 returns to a low state, at the end of the pulse output therefrom, the outputs 230 from gates 206 and 208 continue to hold the lines 102L and 102R low. Any particle detected when the lines 102L and 102R are held low by the outputs 230 from gates 206 and 208, such as the particle resulting in detector outputs 40-5 and 46-5, are prevented from producing a Sort signal from the gates 98L and 98R. Phantom line pulses 98L-4 and 98L-5 are shown to indicate that the inputs to the gate 98L are such as to produce a gate output, but the output remains low because of the low output at other common collector gates 202 and 206, respectively, connected thereto. Sorting is disabled, and remains so, until the circuit is again armed by actuation of arming switch 70. Before rearming the circuit, the tray support 34 is moved to reposition the multiwell tray 32 for receiving the next sorted particle in another tray well.

As noted above, when a particle having selected characteristics for sorting is too close to another particle in the fluid stream 16 for sorting without such other particle also being deflected with the selected particle, an abort signal is produced by abort unit 110, which signal is supplied to both the left and right channels of the sorting logic unit 74 at the inputs to NAND gates 108L and 108R. This situation is depicted in the waveforms of FIG. 3, wherein, after arming switch 70 is momentarily closed to produce an arming pulse 70-4, outputs 40-6 and 46-6 are shown produced by detectors 40 and 46 which outputs fit the windows of analyzers 96-1 and 96-2. Consequently, a left Sort signal 98L-6 is produced at the output from the gate 98L in the manner described above. An adjacent particle in the stream 16 detected by scatter detector 40, results in a scatter detector output 40-7. In response to the scatter detector signal 40-6 and adjacent scatter detector signal 40-7, the abort circuit 110 produces an output pulse 110-7 at line 76 which is supplied as inputs to NAND gates 108L and 108R in both the left and right channels of the system. These abort signals pass through the sorting logic unit 74 and delay unit 84 and simultaneously appear at the inputs 88 and 90 of the deflection logic unit 86. With simultaneous inputs to the exclusive OR gate 118, the gate output does not change states, and no Trigger pulses are produced at the outputs from the AND gates 120L and 120R. Since no Trigger Signal is produced, the flip-flop 214 is not reset. Therefore, after the time delay provided by the one-shot multivibrator 220 output 220-6, the circuit again is in condition for sorting the next detected particle having characteristics fitting the analyzer window settings, without the need to reactivate the arming switch 70. Detector outputs 40-8 and 46-8 which result in a left Sort signal 98L-8, and subsequent sorting operation, are shown in FIG. 3.

For ease in operation of the sorting device, means are provided for direct observation by the operator of the drops at any point in their flight from breakoff from the jet stream 16 to their arrival at the collecting tray, or container 32. To this end there is provided a stroboscopic light unit 136 for illumination of the droplet stream. (See FIG. 1) The light unit 136 is energized by use of the deflection trigger pulses from the deflection logic circuit 86 which are connected thereto through an OR gate 138 and adjustable delay unit 140. With the adjustable delay provided by delay unit 140, the stroboscopic light may be energized for viewing drops at any point along the drop path. Operation of the stroboscopic light 136 also functions to signal the operator that a particle has been sorted from the stream, and that the tray 32 must be repositioned and the sorting circuit rearmed by actuation of switch 70 in preparation for sorting another particle from the stream into a different tray well. Obviously, the Trigger pulses from deflection logic unit 86 may be used to actuate other signaling means, either visual and/or aural, for notifying the operator that a sorting operation has taken place.

Proper positioning of the tray 32 to receive drops sorted from the stream 16 is greatly facilitated by use of the novel movable tray positioning and supporting means 34 shown in FIGS. 4-8, to which Figures reference now is made. The movable tray positioning and supporting means 34 is supported on a platform, or base, 300 carried on sidewalls 302,302 affixed to the sorting device by means not shown. Screws 304 extending through recessed holes in the platform, or base, threadedly engage tapped holes in the upright walls 302,302 to fixedly secure the same to the walls.

Among other components, the tray positioning and supporting means 34 includes a slide, or carriage, 306 movable in one direction along the platform, and a cross slide 308 mounted on the carriage 306 and movable in a transverse direction. In the drawings, perpendicular X and Y axes are shown along the directions which the cross slide 308 and carriage 306, respectively, are movable.

The carriage 306 has a guide rail 310 extending through a slot 312 formed in the base 300 to guide the same for movement along the Y axis. The cross slide 308 is movable along a guide rail 314 at the upper face of the carriage 306 and extending in the X direction. The bottom of the cross slide is formed with a matching groove 316 slidably engageable by the guide rail 314.

A grooved block 318 is attached as by screws 320, to the bottom of platform 300 and underlies the groove 312 formed in the platform. Releasable detent means 322 are provided for releasably locking the carriage 306 at spaced distances along the Y axis. The detent means 322 simply may comprise a ball 324 resiliently biased upwardly by a spring 326 within an aperture, or hole, formed in the grooved section of the block 318 for releasable engagement by the ball with detent holes 328 formed along the bottom of the guide rail 310. The detent holes 328 are spaced apart the same distance as the spacing of the tray wells 32A along the Y direction of the tray. For purposes of illustration only, and not by way of limitation, a 96 well tray 32 is shown which is formed with an 8×12 array of wells 32A. Due to limited space available in the sorting area of the abovementioned prior art gross particle sorting apparatus to which the illustrated individual particle sorting attachments and modifications have been supplied, it is not possible to move the tray 32 sufficiently far rearwardly in the Y direction, for loading of the forward-most rows of wells. Consequently, in the illustrated arrangement, the resilient detent means 322 is provided with only four (4) detent holes 328 for use in loading four rows of tray wells. The tray 32 simply is rotated 180° on the tray positioning and supporting means 34 for sorting into the remaining four rows of wells.

The cross slide 308 also is provided with releasable detent means for releasably locking the same at spaced distances along the carriage 306 in the direction of the X axis, which detent means are identified generally by reference numeral 330. The cross slide detent means 330, which is similar to detent means 322 for the carriage 306 is shown comprising a ball 332 resiliently biased inwardly by a spring 334 within an aperture, or hole, formed in a raised flange 306A extending along the front of the carriage. The ball 332 is releasably engagable with detent holes 336 formed along the front face of the cross slide 308. The detent holes 336 are spaced apart the same distance as the spacing of the tray wells 32A along the X direction of the tray. Twelve adjacent detent holes 336 are provided for each of the twelve wells 32A in a row of tray wells. In addition to the twelve detent holes 336, the cross slide, or carriage, 308 is formed with a calibrating detent hole 336A for use in establishing initial alignment of the tray supporting means in a manner described below.

The tray supporting means 34 includes a container, or tray holder 338 upon which the tray 32 rests, which holder includes upright walls 340 on the upper face thereof for positioning the tray 32 on the holder. An arm 342 connects the tray holder 338 to the cross slide, or carriage, 308. Releasable locking means, comprising a bolt 344 extending through an elongated slot 346 in the connecting arm 342 and threadedly engaging a tapped hole in the tray holder 338, releasably locks the tray holder 338 to the inner end of the connecting arm. A guide rail 348 on the upper face of the tray holder, and cooperating groove in the bottom face of the arm 342, limit movement of the tray holder 338 along the Y direction when the bolt 344 is released. Another releasable locking means, comprising a bolt 350 extending through an elongated slot 352 in the cross slide 308 and threadedly engaging a tapped hole in the arm 342, releasably locks the arm 342 to the cross slide 308. A lap connection is provided between the arm 342 and cross slide 308 which allows for relative movement therebetween along the X direction when the bolt 350 is released, or loosened. It will be apparent, then, that adjustment of the tray holder 338 in the Y and X directions relative to the cross slides, or carriages, 306 and 308 is possible upon release of the fastening means 344 and 350, respectively.

For use in establishing initial alignment of the tray holder 338 relative to drops deflected from the drop stream, the holder 338 is provided with a tab 354 having a target thereon, here comprising an aperture, or hole, 356 formed in the tab. The hole 356, which may be of substantially the same diameter as a tray well, is located substantially the same distance "d" from the adjacent tray well 32A as the distance "d" between the alignment detent hole 336A and adjacent detent hole 336. The hole 356 serves as a target for particles sorted from the drop stream, for use in properly positioning the tray holder 338 relative to the carriages before the start of an individual particle sorting operation. With the detent means 322 and 330 in alignment position, and bolts 344 and 350 loosened, the tray holder 338 is adjusted so that drops separated from the stream enter the target hole 356. The bolts then are retightened and the tray holder is positioned so that drops separated from the stream enter the desired tray well. A handle 358 is provided on the connecting arm 342 which is readily gripped by the operator for use in step positioning the tray holder in the X and Y directions along the supporting base 300.

The stream catcher 30, which may be of the same construction as the stream catcher shown in the above-mentioned article entitled "Individual Cell Sorting" is shown comprising a tube 360 closed at one end 362 and connected at the other end to a vacuum source, not shown. The tube is adjustable positioned relative to the drop stream by use of suitable supporting means, not shown. A slot 364 is formed in the top of the tube through which a small plate 366 extends. The plate is attached to one edge of the slot and extends upwardly at an angle to a vertical plane. The upper edge of the plate is beveled, with the beveled surface extending substantially vertically. The mainstream of drops is intercepted by the plate 366 and aspirated into the stream catcher tube 360. With the stream catcher 30 in the illustrated position, charged drops are deflected to the left, into the tray wells. If desired, the stream catcher could be positioned to intercept charged drops, with uncharged drops passing into the tray wells. Such operation would require modification of the deflection logic circuit to provide for such drop charging. In the claims, terminology such as, "deflection of selected drops from the mainstream of drops" is intended to include deflection resulting from any drop charge differences, and not only the illustrated sorting provided by charging of selected drops and non-charging of all other drops.

Although the operation of the sorter for individual particle sorting is believed to be apparent, a brief description thereof now will be given. The stream catcher 30 and tray positioning and supporting means 34 are attached to the sorter, and the on-off switch 68 for individual cell sorting is turned on. The single channel analyzers 96-1 and 96-2 for the left channel are set for sorting of the desired particles from the jet stream 16. The stream catcher 30 is positioned to catch all undeflected drops. A multiwell tray 32 is positioned on the tray holder 338 inside the walls 340. By use of the handle 358, the tray positioning and sorting means 34 is moved to the initial aligning position; i.e. with the carriage 306 in the forward-most position, and the cross slide 308 to the right-most position wherein detent ball 332 engages detent hole 336A. Then the arming switch 70 is acuated for, essentially, enabling the pulse charging unit 64 for charging a drop containing a particle of the selected type. The charged drop, or small group of charged drops, is deflected toward the target hole 356. Adjustable delay means 140 are adjusted for illumination of the separated drop, or drops, by the strobe light 136 as the drops enter the target hole. If the charged drops fail to enter the target hole, the screw 344 and/or screw 350 are loosened and the tray holder 338 is adjusted to position the target hole in the path of the deflected drops. Repeated operation of the arming switch 70 for repeated drop deflection often is required during the alignment process.

Once properly aligned, the screws 344 and/or 350 are retightened, and the tray holder 338 is moved to position one of the tray wells in the deflected drop path. The detents 322 and 330 assure proper positioning of the tray holder, and tray, for catching the deflected drops in the tray wells. Operation of the strobe light 136 by trigger pulses from the sorting unit 64 signals the operator that sorting of a particles has occurred. The tray positioning and supporting means 34 is moved by the operator to position the next tray well in the deflected stream path, and the arm switch 70 is again operated to condition the sorter for another individual particle sorting operation. Obviously, other visual, or audible means under control of trigger pulses may be employed for signaling when drop charging has occured for the particle sort. With the illustrated arrangement, when the rear four rows or wells have been supplied with deflected particles, the tray 32 is rotated 180° in order to fill the remaining four rows.

The invention having been described in detail in accordance with requirements of the Patent Statues, various changes and modifications will suggest themselves to those skilled in this art, which changes and modifications are intended to fall within the spirit and scope of the invention as defined in the appended claims.

We claim:

1. In apparatus for particle sorting having a nozzle for producing a stream of particle-containing fluid, means for jetting the stream from the nozzle, means for modulating the velocity of the stream to break the jet stream into uniform discrete drops, detector means for detecting particles in the stream, pulse charging circuit means responsive to said detector means for producing a delayed drop charge for charging selected drops in response to selected outputs from said detector means, and means for deflecting charged drops an amount related to the drop charge, the improvement comprising the combination therewith of means adapting the apparatus for individual, non-pooled, particle sorting comprising,
   means responsive to said selected outputs from the detector means for temporarily preventing subsequent selected outputs from said detector means from producing a drop charge output from the pulse charging circuit for a predetermined time period, and
   resettable means responsive to drop charging operation of said pulse charging circuit for preventing subsequent drop charging operation until said resettable means are reset.

2. In apparatus for particle sorting as defined in claim 1 wherein said pulse charging circuit means includes means for developing a sort signal in response to selected outputs from said detector means, and signal delay means for delaying sort signals for delayed drop charging operation of the pulse charging circuit, the improvement wherein said temporarily preventing means are responsive to undelayed sort signals, and
   said resettable means are responsive to delayed sort signals.

3. In apparatus for particle sorting as defined in claim 2 wherein said means for developing a sort signal, said temporary preventing means, and said resettable circuit means include open collector gates having interconnected gate outputs for control of said means for developing a sort signal by said temporary preventing means and said resettable circuit means.

4. In apparatus for particle sorting having a nozzle for producing a stream of particle-containing fluid, means for jetting the stream from the nozzle, means for modulating the velocity of the stream to break the jet stream into discrete drops, detector means for detecting particles in the stream, means for producing a sort signal in response to selected outputs from said detector means, time delay means for time delay of said sort signal to allow for travel of a particle from a point of detection to the point at which the stream breaks into drops, pulse charging means for charging drops breaking from the stream, means responsive to said time-delayed sort signal for triggering operation of the pulse charging means to change the charge supplied to selected drops breaking from the stream, and means for deflecting charged drops an amount related to the drop charge, the combination therewith of means adapting the apparatus for individual, non-pooled, sorting of selected particles comprising,     means responsive to said sort signal for temporarily disabling operation of said sort signal producing means for a period of time at least as long as the delay provided by said time delay means, and     resettable circuit means for continuing to disable operation of said sort signal producing means upon triggering of said pulse charging means until said resettable circuit means is reset.

5. In apparatus for particle sorting as defined in claim 4 which includes abort circuit means for preventing time-delayed sort signals from triggering operation of said pulse charging means when a particle which results in the production of a sort signal is too close to another detected particle for separation therefrom.

6. In apparatus for particle sorting as defined in claim 5 wherein said resettable circuit means are responsive to unaborted time-delayed sort signals which trigger operation of said pulse charging means.

7. In apparatus for particle sorting as defined in claim 6 wherein said pulse charging means comprises a pulse amplifier having an output connected to an electrode in contact with the stream of particle-containing fluid.

8. In apparatus for particle sorting as defined in claim 4 wherein said temporarily disabling means comprises a one-shot which is triggered by said sort signal.

9. In apparatus for particle sorting as defined in claim 4 wherein said resettable circuit means comprises a flip-flop which is set by said means for triggering operation of said pulse charging means, and     means including a switch for resetting said flip-flop.

10. In apparatus for particle sorting as defined in claim 9 wherein said switch means is of the manually operated type for manual control thereof by an operator.

11. In a method of separating individual particles from other particles contained in a fluid stream and maintaining the separation without pooling of certain particles the combination comprising,     producing a flow stream which includes particle-containing fluid,     jetting the fluid flow stream,     modulating the jet stream velocity in the direction of the stream axis to break the stream into discrete drops,     detecting particles in the stream and producing a sort signal in response to the detection of certain particles,     triggering operation of a pulse generator by a time delayed sort signal for charging the jet stream while drops which contain a detected certain particle break from the jet stream,     deflecting charged drops in an amount related to the drop charge,     in response to production of a sort signal, temporarily preventing production of subsequent sort signals, and     continuing for an indefinite period of time to prevent production of subsequent sort signals whenever a delayed sort signal triggers operation of the pulse generator.

12. In a method of separating individual particles from other particles as defined in claim 11 including, resuming particle separation operation under control of switch means.

13. In a method of separating individual particles from other particles as defined in claim 12 wherein said switch means are manually operated for manual control of the operation.

14. In a method of separating individual particles from other particles as defined in claim 12 including,     catching drops which contain a detected certain particle in the well of a multiwell tray, and     repositioning said tray before resuming particle separation operation to catch other drops in other wells of the tray.

15. Particle sorting apparatus for loading containers with single particles for culturing, cloning, or the like, comprising,     a nozzle,     means for jetting a stream of particle-containing fluid from the nozzle,     means for modulating the velocity of the stream to break the jet stream into discrete drops,     detector means for detecting particles in the stream,     pulse charging means for supplying drops with different drop charges,     means for deflecting charged drops an amount related to the drop charge,     a stream catcher for catching drops not separated from the drop stream,     manually controlled means for enabling operation of the pulse charging means to render the same responsive to the detector means for sorting a single detected particle contained in a drop from the stream of drops,     means for automatically disabling operation of the pulse charging means following sorting of the single particle from the stream,     a movable tray support for the support of a multiwell tray into which drops separated from the drop stream are sorted, and     releasable detent means for releasably locking said tray support at a plurality of spaced positions for catching drops separated from the drop stream in the tray wells.

16. Particle sorting apparatus as defined in claim 15 including, means forming a target on said movable tray support for use in initial alignment of the tray support with respect to drops separated from the drop stream.

17. Particle sorting apparatus as defined in claim 16 wherein said target is located outside of the area of support for the tray, and     means including said releasable detent means for releasably locking said tray support at a target alignment position.

18. Particle sorting apparatus as defined in claim 16 wherein said target comprises an aperture formed in said tray support.

19. Particle sorting apparatus as defined in claim 15 wherein said tray support is manually movable.

20. In a particle sorter of the type which includes means for producing a stream of discrete drops, some of which contain a particle to be sorted from the drop stream into a container, the improvement comprising,     a movable container support for support of a container into which particle-containing drops separated from the drop stream are to be loaded,     a target on said movable container support for use in initial alignment of the container support relative to drops separated from the drop stream, and     releasable detent means for releasably locking said container support at an alignment position and at a drop-catching position for receiving drops separated from the drop stream in a container supported thereon.

21. Particle sorting apparatus as defined in claim 20 wherein the container support is adapted for support of a multiwell tray, and
said releasable detent means releasably lock the container support at a plurality of spaced positions for receiving drops in individual tray wells.

22. A tray supporting mechanism for movable support of a multiwell tray for use with a particle sorting system of the type which includes means for producing a stream of discrete drops, some of which drops contain particles to be sorted from the stream by separation of certain particle-containing drops from the drop stream, said mechanism comprising
a base toward which said drop stream is directed,
carriage means on the base movable in at least one direction therealong,
a tray holder attached to said carriage means for support of a multiwell tray at a fixed location on the holder, and
releasable detent means for releasably locking said carriage means at spaced positions along said at least one direction for positioning tray wells to receive drops separated from the drop stream,
said carriage means being manually movable for manual positioning thereof and the attached tray holder.

23. A tray supporting mechanism for movable support of a multiwell tray for use with a particle sorting system of the type which includes means for producing a stream of discrete drops, some of which drops contain particles to be sorted from the stream by separation of certain particle-containing drops from the drop stream, said mechanism comprising
a base toward which said drop stream is directed,
carriage means on the base movable in at least one direction therealong,
a tray holder attached to said carriage means for support of a multiwell tray at a fixed location on the holder, and
releasable detent means for releasably locking said carriage means at spaced positions along said at least one direction for positioning tray wells to receive drops separated from the drop stream,
said tray holder being attached to said carriage means by releasable fastening means for adjustable positioning of the tray holder along at least said one direction relative to said carriage means in the released condition of said fastening means for initial alignment purposes.

24. A tray supporting mechanism as defined in claim 22 wherein said carriage means are movable along perpendicular X-Y directions and said releasable detent means include first and second means for releasably locking said carriage means at spaced positions along said respective X and Y directions.

25. A tray supporting mechanism as defined in claim 22 including a target formed on the tray holder for use in initial alignment of the tray holder relative to said carriage means to assure that separated drops enter tray wells during sorting operation.

26. A tray supporting mechanism as defined in claim 25 wherein said releasable detent means includes means for positioning said carriage for initial alignment of the tray holder target relative to the drops separated from the stream.

27. A tray supporting mechanism as defined in claim 22 wherein
said carriage means comprise a Y carriage movable along the base and an X carriage movable along the Y carriage in perpendicular Y and X directions, respectively, and
said releasable detent means includes a first releasable detent for releasably locking said Y carriage at spaced positions along the Y direction and a second releasable detent for releasably locking said X carriage at spaced positions along the X direction.

28. A tray supporting mechanism for movable support of a multiwell tray for use with a particle sorting system of the type which includes means for producing a stream of discrete drops, some of which drops contain particles to be sorted from the stream by separation of certain particle-containing drops from the drop stream, said mechanism comprising
a base toward which said drop stream is directed,
carriage means on the base comprising a Y carriage movable along the base and an X carriage movable along the Y carriage in perpendicular Y and X directions, respectively,
a tray holder attached to said carriage means for support of a multiwell tray at a fixed location on the holder, and
releasable detent means for releasably locking said carriage means at spaced positions along said X and Y directions for positioning tray wells to receive drops separated from the drop stream, said releasable detent means including a first releasable detent for releasably locking said Y carriage at spaced positions along the Y direction and a second releasable detent for releasably locking said X carriage at spaced positions along the X direction, said first releasable detent including means for releasably locking said Y carriage at positions numbering one-half the total number of rows of tray wells and said second releasable detent means includes means for releasably locking said X carriage at positions numbering the total number of columns of tray wells.

29. A tray supporting mechanism for movable support of a multiwell tray for use with a particle sorting system of the type which includes means for producing a stream of discrete drops, some of which drops contain particles to be sorted from the stream by separation of certain particle-containing drops from the drop stream, said mechanism comprising
a base toward which said drop stream is directed,
carriage means on the base comprising a Y carriage movable along the base and an X carriage movable along the Y carriage in perpendicular Y and X directions, respectively,
a tray holder attached to said carriage means for support of a multiwell tray at a fixed location on the holder, and
releasable detent means for releasably locking said carriage means at spaced positions along said X and Y directions for positioning tray wells to receive drops separated from the drop stream, said releasable detent means including a first releasable detent for releasably locking said Y carriage at spaced positions along the Y direction and a second releasable detent for releasably locking said X carriage at spaced positions along the X direction, said second releasable detent means including means for releasably locking said X carriage at an additional position for initial alignment of the tray holder relative to drops separated from the stream.

30. A tray supporting mechanism as defined in claim 29 wherein said tray holder is formed with a target for use in said initial alignment of the tray holder relative to drops separated from the stream.

* * * * *